US008481265B2

(12) United States Patent
Peytavi et al.

(10) Patent No.: US 8,481,265 B2
(45) Date of Patent: Jul. 9, 2013

(54) CONCENTRATION AND ENRICHMENT OF MICROBIAL CELLS AND MICROBIAL NUCLEIC ACIDS FROM BODILY FLUIDS

(75) Inventors: Régis Peytavi, Cabestany (FR); Ann Huletsky, Québec (CA); Lucile Belley-Montfort, Stoneham (CA); Isabelle Martineau, Québec (CA)

(73) Assignee: Universite Laval, Quebec (CA)

( * ) Notice: Subject to any disclaimer, the term of this patent is extended or adjusted under 35 U.S.C. 154(b) by 186 days.

(21) Appl. No.: 12/671,741

(22) PCT Filed: Aug. 1, 2008

(86) PCT No.: PCT/CA2008/001414
§ 371 (c)(1),
(2), (4) Date: Jul. 27, 2010

(87) PCT Pub. No.: WO2009/015484
PCT Pub. Date: Feb. 5, 2009

(65) Prior Publication Data
US 2011/0294128 A1    Dec. 1, 2011

Related U.S. Application Data

(60) Provisional application No. 60/935,244, filed on Aug. 2, 2007, provisional application No. 61/008,292, filed on Dec. 20, 2007.

(51) Int. Cl.
*C12Q 1/68* (2006.01)
*C12Q 1/24* (2006.01)
*C12P 19/34* (2006.01)

(52) U.S. Cl.
USPC ............................ 435/6.12; 435/91.2; 435/30

(58) Field of Classification Search
USPC ......................... 435/6.12, 91.2, 30
See application file for complete search history.

(56) References Cited

U.S. PATENT DOCUMENTS

| 2,301,787 | A |   | 11/1942 | Nord |   |
|---|---|---|---|---|---|
| 3,883,425 | A |   | 5/1975 | Dorn |   |
| 4,014,745 | A | * | 3/1977 | Fletcher et al. | 435/8 |
| 4,164,449 | A |   | 8/1979 | Dorn et al. |   |
| 4,243,534 | A |   | 1/1981 | Bulbenko |   |
| 4,666,850 | A |   | 5/1987 | Mehl et al. |   |
| 4,994,378 | A |   | 2/1991 | Berger et al. |   |
| 5,426,027 | A | * | 6/1995 | Lott et al. | 435/6.13 |
| 5,501,960 | A |   | 3/1996 | Dorn |   |
| 5,622,827 | A | * | 4/1997 | McAllister et al. | 435/6.12 |
| 7,547,526 | B2 | * | 6/2009 | Ladisch et al. | 435/30 |

FOREIGN PATENT DOCUMENTS

| EP | 0571203 A1 | 11/1993 |
|---|---|---|
| EP | 0 745 849 | 12/1996 |
| EP | 0745849 A2 | 12/1996 |
| EP | 1 422 509 | 5/2004 |
| EP | 1 422 509 A1 | 5/2004 |

OTHER PUBLICATIONS

Loncarevic et al. Letters in Applied Microbiology, 2005, vol. 41, p. 186-189.*
Extended European Search Report from European Patent Application No. 08783325.7, dated Mar. 16, 2011 (date of mailing of report) and Feb. 21, 2011 (date of completion of search).
Certain et al., "*Plasmodium falciparum*: A Novel Method for Analyzing Haplotypes in Mixed Infections," Exp. Parasitol. 115:223-241, 2007.
Han et al., "Detection of Four *Plasmodium* Species by Genus- and Species-Specific Loop-Mediated Isothermal Amplification for Clinical Diagnosis," J. Clin. Microbiol. 45:2521-2528, 2007.
International Search Report from International Application No. PCT/CA2008/001414, dated Sep. 30, 2008 (date of completion of search) and Oct. 19, 2008 (date of mailing of report).
International Preliminary Report on Patentability from International Application No. PCT/CA2008/001414, dated Feb. 2, 2010.
Al-Soud et al., "Purification and Characterization of PCR-Inhibitory Components in Blood Cells," J. Clin. Microbiol. 39:485-493, 2001.
Barr et al., "ISCOMs and Other Saponin Based Adjuvants," Adv. Drug Deliv. Rev. 32:247-271, 1998.
Bernhardt et al., "Detection of Bacteria in Blood by Centrifugation and Filtration," J. Clin. Microbiol. 29:422-425, 1991.
Bougnoux et al., "Serum Is More Suitable than Whole Blood for Diagnosis of Systemic Candidiasis by Nested PCR," J. Clin. Microbiol. 37:925-930, 1999.
Cockerill et al., "Clinical Comparison of Difco ESP, Wampole Isolator, and Becton Dickinson Septi-Chek Aerobic Blood Culturing Systems," J. Clin. Microbiol. 34:20-24, 1996.
Daar et al., "Top Ten Biotechnologies for Improving Health in Developing Countries," Nat. Genet. 32:229-232, 2002.
Francis et al., "The Biological Action of Saponins in Animal Systems: A Review," Br. J. Nutr. 88:587-605, 2002.
Grossi et al., "Antimicrobial Treatment of Sepsis," Surg. Infect. 7 Suppl. 2: S87-S91, 2006.
Güçlü-Üstündağ et al., "Saponins: Properties, Applications and Processing," Crit. Rev. Food Sci. Nutr. 47:231-258, 2007.
Henry et al., "Microbiological and Clinical Evaluation of the Isolator Lysis-Centrifugation Blood Culture Tube," J. Clin. Microbiol. 17:864-869, 1983.
Hoorfar et al., "Diagnostic PCR: Making Internal Amplification Control Mandatory," J. Appl. Microbiol. 96:221-222, 2004.
Jonsson et al., "Theoretical Aspects of Detection of Bacteraemia as a Function of the Volume of Blood Cultured," APMIS 101:595-601, 1993.
Jordan et al., "Real-Time Polymerase Chain Reaction for Detecting Bacterial DNA Directly from Blood of Neonates Being Evaluated for Sepsis," J. Mol. Diagn. 7:575-581, 2005.

(Continued)

*Primary Examiner* — Kenneth R. Horlick
*Assistant Examiner* — Joyce Tung
(74) *Attorney, Agent, or Firm* — Clark & Elbing LLP

(57) ABSTRACT

The present invention relates to a method for isolating microorganisms and/or microorganisms nucleic acids from a bodily fluid that may comprise or may be suspected to comprise microorganisms and/or host cells and/or host cells debris. Microorganisms nucleic acids may further be isolated by lysing the isolated microorganisms. The present invention also relates to a method for detecting microorganisms in a bodily fluid. The present invention further relates to a saponin formulation and its use.

20 Claims, 2 Drawing Sheets

OTHER PUBLICATIONS

Kiehn et al., "Comparative Recovery of Bacteria and Yeasts from Lysis-Centrifugation and a Conventional Blood Culture System," J. Clin. Microbiol. 18:300-304, 1983.

Leconte et al., "Protective Effect of Iridals from Saponin Injury in *Candida Albicans* Cells," Phytochemistry 44:575-579, 1997.

Link et al., "Beyond Toothpicks: New Methods for Isolating Mutant Bacteria," Nat. Rev. Microbiol. 5:680-688, 2007.

Loeffler et al., "Automated Extraction of Genomic DNA from Medically Important Yeast Species and Filamentous Fungi by Using the MagNA Pure LC System," J. Clin. Microbiol. 40:2240-2243, 2002.

McLaughlin et al., "Clinical Laboratory Comparison of Lysis-Centrifugation and BACTEC Radiometric Blood Culture Techniques," J. Clin. Microbiol. 18:1027-1031, 1983.

Melzig et al., "Investigations of the Mechanism of Membrane Activity of Selected Triterpenoid Saponins," Planta Med. 67:43-48, 2001.

Metzger et al., "Direct Identification of MRSA and $MLS_B$ Phenotypes in *Staphylococcus aureus* Using Small Numbers of Immobilized Cells," ASM general meeting, C-005, 2008.

Metzger et al., "Direct Detection and Enumeration of Viable Bacteria in Human Bronchoalveolar Lavage Specimens Using Automated Growth Rate Analysis," ASM general meeting, C-145, 2008.

Milgate et al., "The Nutritional & Biological Significance of Saponins," Nutrition Research 15:1223-1249, 1995.

Mitra et al., "Micellar Properties of Quillaja Saponin. 1. Effects of Temperature, Salt, and pH on Solution Properties," J. Agric. Food Chem. 45:1587-1595, 1997.

Murray et al., "Clinical Comparison of the Recoveries of Bloodstream Pathogens in Septi-Chek Brain Heart Infusion Broth with Saponin, Septi-Chek Tryptic Soy Broth, and the Isolator Lysis-Centrifugation System," J. Clin. Microbiol. 29:901-905, 1991.

Okubo et al., "Oxygen-Radical-Scavenging Activity of DDMP-Conjugated Saponins and Physiological Role in Leguminous Plant," Adv. Exp. Med. Biol. 405:141-154, 1996.

San Martin et al., "Quality Control of Commercial Quillaja (*Quillaja Saponaria* Molina) Extracts by Reverse Phase HPLC," J. Sci. Food Agric. 80:2063-2068, 2000.

Takechi et al., "Biological Activities of Synthetic Saponins and Cardiac Glycosides," Phytother. Res. 17:83-85, 2003.

Taylor, "Routine Laboratory Diagnosis of Continuous Ambulatory Peritoneal Dialysis Peritonitis using Centrifugation/Lysis and Saponin-Containing Media," Eur. J. Clin. Microbiol. Infect. Dis. 13:249-252, 1994.

Weibel et al., "Microfabrication Meets Microbiology," Nat. Rev. Microbiol. 5:209-218, 2007.

White et al., "The Evolution and Evaluation of a Whole Blood Polymerase Chain Reaction Assay for the Detection of Invasive Aspergillosis in Hematology Patients in a Routine Clinical Setting," Clin. Infect. Dis. 42:479-486, 2006.

Rubin et al., "Comparison of the Du Pont Isolator 1.5 Microbial Tube and Trypticase Soy Broth for the Recovery of *Haemophilus influenzae* Type b in Experimental Bacteremia," Journal of Clinical Microbiology, vol. 22, No. 5: 815-818, Nov. 1985.

\* cited by examiner

SEQUENCE LISTING

```
<160> NUMBER OF SEQ ID NOS: 32

<210> SEQ ID NO 1
<211> LENGTH: 21
<212> TYPE: DNA
<213> ORGANISM: Artificial Sequence
<220> FEATURE:
<223> OTHER INFORMATION: Sequence is completely synthesized

<400> SEQUENCE: 1
acttgtccac gttsgatrtc t                                               21

<210> SEQ ID NO 2
<211> LENGTH: 23
<212> TYPE: DNA
<213> ORGANISM: Artificial Sequence
<220> FEATURE:
<223> OTHER INFORMATION: Sequence is completely synthesized

<400> SEQUENCE: 2
aattaatggc tgcwgttgay gaa                                             23

<210> SEQ ID NO 3
<211> LENGTH: 22
<212> TYPE: DNA
<213> ORGANISM: Artificial Sequence
<220> FEATURE:
<223> OTHER INFORMATION: Sequence is completely synthesized

<400> SEQUENCE: 3
atcccaactc cagaacgtga ya                                              22

<210> SEQ ID NO 4
<211> LENGTH: 18
<212> TYPE: DNA
<213> ORGANISM: Artificial Sequence
<220> FEATURE:
<223> OTHER INFORMATION: Sequence is completely synthesized

<400> SEQUENCE: 4
tgggaagcga aaatcctg                                                   18

<210> SEQ ID NO 5
<211> LENGTH: 19
<212> TYPE: DNA
<213> ORGANISM: Artificial Sequence
<220> FEATURE:
<223> OTHER INFORMATION: Sequence is completely synthesized

<400> SEQUENCE: 5
cagtacaggt agacttctg                                                  19

<210> SEQ ID NO 6
<211> LENGTH: 18
<212> TYPE: DNA
<213> ORGANISM: Artificial Sequence
<220> FEATURE:
<223> OTHER INFORMATION: Sequence is completely synthesized
```

```
<400> SEQUENCE: 6
aactggctgg cttcctgg                                                  18

<210> SEQ ID NO 7
<211> LENGTH: 23
<212> TYPE: DNA
<213> ORGANISM: Artificial Sequence
<220> FEATURE:
<223> OTHER INFORMATION: Sequence is completely synthesized
<220> FEATURE:
<221> NAME/KEY: misc_feature
<222> LOCATION: (12)..(12)
<223> OTHER INFORMATION: n is for inosine

<400> SEQUENCE: 7
actggygttg anatgttccg yaa                                            23

<210> SEQ ID NO 8
<211> LENGTH: 23
<212> TYPE: DNA
<213> ORGANISM: Artificial Sequence
<220> FEATURE:
<223> OTHER INFORMATION: Sequence is completely synthesized
<220> FEATURE:
<221> NAME/KEY: misc_feature
<222> LOCATION: (9)..(9)
<223> OTHER INFORMATION: n is for inosine

<400> SEQUENCE: 8
acgtcagtng tacggaarta gaa                                            23

<210> SEQ ID NO 9
<211> LENGTH: 23
<212> TYPE: DNA
<213> ORGANISM: Artificial Sequence
<220> FEATURE:
<223> OTHER INFORMATION: Sequence is completely synthesized

<400> SEQUENCE: 9
acaggtgttg aaatgttccg taa                                            23

<210> SEQ ID NO 10
<211> LENGTH: 23
<212> TYPE: DNA
<213> ORGANISM: Artificial Sequence
<220> FEATURE:
<223> OTHER INFORMATION: Sequence is completely synthesized

<400> SEQUENCE: 10
acgtctgttg tacggaagta gaa                                            23

<210> SEQ ID NO 11
<211> LENGTH: 23
<212> TYPE: DNA
<213> ORGANISM: Artificial Sequence
<220> FEATURE:
<223> OTHER INFORMATION: Sequence is completely synthesized

<400> SEQUENCE: 11
caggaatcga aatgttcaga aag                                            23

<210> SEQ ID NO 12
<211> LENGTH: 23
<212> TYPE: DNA
<213> ORGANISM: Artificial Sequence
<220> FEATURE:
<223> OTHER INFORMATION: Sequence is completely synthesized
```

<400> SEQUENCE: 12
acgtctgttg ttctgaagta gaa                                              23

<210> SEQ ID NO 13
<211> LENGTH: 23
<212> TYPE: DNA
<213> ORGANISM: Artificial Sequence
<220> FEATURE:
<223> OTHER INFORMATION: Sequence is completely synthesized

<400> SEQUENCE: 13
acctccatcg agatgttcaa caa                                              23

<210> SEQ ID NO 14
<211> LENGTH: 18
<212> TYPE: DNA
<213> ORGANISM: Artificial Sequence
<220> FEATURE:
<223> OTHER INFORMATION: Sequence is completely synthesized

<400> SEQUENCE: 14
ggtggtgcgg aagtagaa                                                    18

<210> SEQ ID NO 15
<211> LENGTH: 23
<212> TYPE: DNA
<213> ORGANISM: Artificial Sequence
<220> FEATURE:
<223> OTHER INFORMATION: Sequence is completely synthesized

<400> SEQUENCE: 15
acaggagttg agatgttccg taa                                              23

<210> SEQ ID NO 16
<211> LENGTH: 23
<212> TYPE: DNA
<213> ORGANISM: Artificial Sequence
<220> FEATURE:
<223> OTHER INFORMATION: Sequence is completely synthesized

<400> SEQUENCE: 16
acgtcagttg tacgaacata gaa                                              23

<210> SEQ ID NO 17
<211> LENGTH: 21
<212> TYPE: DNA
<213> ORGANISM: Artificial Sequence
<220> FEATURE:
<223> OTHER INFORMATION: Sequence is completely synthesized
<220> FEATURE:
<221> NAME/KEY: misc_feature
<222> LOCATION: (7)..(7)
<223> OTHER INFORMATION: n is inosine

<400> SEQUENCE: 17
ggtwgtngct gcgactgacg g                                                21

<210> SEQ ID NO 18
<211> LENGTH: 20
<212> TYPE: DNA
<213> ORGANISM: Artificial Sequence
<220> FEATURE:
<223> OTHER INFORMATION: Sequence is completely synthesized

<400> SEQUENCE: 18
tcaatcgcac gctctggttc                                                  20

```
<210> SEQ ID NO 19
<211> LENGTH: 19
<212> TYPE: DNA
<213> ORGANISM: Artificial Sequence
<220> FEATURE:
<223> OTHER INFORMATION: Sequence is completely synthesized

<400> SEQUENCE: 19
aacgtggtca agtwttagc                                                    19

<210> SEQ ID NO 20
<211> LENGTH: 20
<212> TYPE: DNA
<213> ORGANISM: Artificial Sequence
<220> FEATURE:
<223> OTHER INFORMATION: Sequence is completely synthesized

<400> SEQUENCE: 20
gtacggaart agaattgwgg                                                   20

<210> SEQ ID NO 21
<211> LENGTH: 21
<212> TYPE: DNA
<213> ORGANISM: Artificial Sequence
<220> FEATURE:
<223> OTHER INFORMATION: Sequence is completely synthesized
<220> FEATURE:
<221> NAME/KEY: misc_feature
<222> LOCATION: (8)..(8)
<223> OTHER INFORMATION: n is inosine
<220> FEATURE:
<221> NAME/KEY: misc_feature
<222> LOCATION: (11)..(11)
<223> OTHER INFORMATION: n is inosine

<400> SEQUENCE: 21
gtggratngc ngcctttatc g                                                 21

<210> SEQ ID NO 22
<211> LENGTH: 20
<212> TYPE: DNA
<213> ORGANISM: Artificial Sequence
<220> FEATURE:
<223> OTHER INFORMATION: Sequence is completely synthesized
<220> FEATURE:
<221> NAME/KEY: misc_feature
<222> LOCATION: (3)..(3)
<223> OTHER INFORMATION: n is inosine

<400> SEQUENCE: 22
atngcctgrc tcatcatacg                                                   20

<210> SEQ ID NO 23
<211> LENGTH: 24
<212> TYPE: DNA
<213> ORGANISM: Artificial Sequence
<220> FEATURE:
<223> OTHER INFORMATION: Sequence is completely synthesized
<220> FEATURE:
<221> NAME/KEY: misc_feature
<222> LOCATION: (19)..(19)
<223> OTHER INFORMATION: n is inosine

<400> SEQUENCE: 23
caagatggay tcygtyaant ggga                                              24

<210> SEQ ID NO 24
<211> LENGTH: 24
```

```
<212> TYPE: DNA
<213> ORGANISM: Artificial Sequence
<220> FEATURE:
<223> OTHER INFORMATION: Sequence is completely synthesized

<400> SEQUENCE: 24
catcttgcaa tggcaatctc aatg                                              24

<210> SEQ ID NO 25
<211> LENGTH: 24
<212> TYPE: DNA
<213> ORGANISM: Artificial Sequence
<220> FEATURE:
<223> OTHER INFORMATION: Sequence is completely synthesized

<400> SEQUENCE: 25
catcttgtaa tggtaatctt aatg                                              24

<210> SEQ ID NO 26
<211> LENGTH: 22
<212> TYPE: DNA
<213> ORGANISM: Artificial Sequence
<220> FEATURE:
<223> OTHER INFORMATION: Sequence is completely synthesized
<220> FEATURE:
<221> NAME/KEY: misc_feature
<222> LOCATION: (11)..(11)
<223> OTHER INFORMATION: n is inosine

<400> SEQUENCE: 26
gttccagacy nccaagtatg ag                                                22

<210> SEQ ID NO 27
<211> LENGTH: 23
<212> TYPE: DNA
<213> ORGANISM: Artificial Sequence
<220> FEATURE:
<223> OTHER INFORMATION: Sequence is completely synthesized

<400> SEQUENCE: 27
atttcgttgt aacgatcctc gga                                               23

<210> SEQ ID NO 28
<211> LENGTH: 24
<212> TYPE: DNA
<213> ORGANISM: Artificial Sequence
<220> FEATURE:
<223> OTHER INFORMATION: Sequence is completely synthesized

<400> SEQUENCE: 28
gatttcgttg taacgatcct gaga                                              24

<210> SEQ ID NO 29
<211> LENGTH: 23
<212> TYPE: DNA
<213> ORGANISM: Artificial Sequence
<220> FEATURE:
<223> OTHER INFORMATION: Sequence is completely synthesized

<400> SEQUENCE: 29
atttcgttgt aacggtcctc aga                                               23

<210> SEQ ID NO 30
<211> LENGTH: 20
<212> TYPE: DNA
<213> ORGANISM: Artificial Sequence
<220> FEATURE:
<223> OTHER INFORMATION: Sequence is completely synthesized
```

```
<220> FEATURE:
<221> NAME/KEY: misc_feature
<222> LOCATION: (11)..(11)
<223> OTHER INFORMATION: n is inosine

<400> SEQUENCE: 30
tgatgccgrt ngaagacgtg                                              20

<210> SEQ ID NO 31
<211> LENGTH: 20
<212> TYPE: DNA
<213> ORGANISM: Artificial Sequence
<220> FEATURE:
<223> OTHER INFORMATION: Sequence is completely synthesized

<400> SEQUENCE: 31
agyttgcgga acatttcaac                                              20

<210> SEQ ID NO 32
<211> LENGTH: 19
<212> TYPE: DNA
<213> ORGANISM: Artificial Sequence
<220> FEATURE:
<223> OTHER INFORMATION: Sequence is completely synthesized

<400> SEQUENCE: 32
gtgggaagcg aaaatcctg                                               19
```

CONCENTRATION AND ENRICHMENT OF MICROBIAL CELLS AND MICROBIAL NUCLEIC ACIDS FROM BODILY FLUIDS

CROSS-REFERENCE TO RELATED APPLICATIONS

This application is the U.S. national stage filing under 35 U.S.C. §371 of international application PCT/CA2008/001414, filed Aug. 1, 2008, which claims benefit of U.S. Provisional Patent Application No. 60/935,244, filed Aug. 2, 2007, and U.S. Provisional Patent Application No. 61/008,292, filed Dec. 20, 2007.

FIELD OF INVENTION

This invention relates to the concentration and enrichment of microbial cells and microbial nucleic acids from bodily fluids. The invention also relates to detection of microbial cells in bodily fluids.

BACKGROUND OF THE INVENTION

The development of rapid molecular diagnostic tests for human infections is the most highly rated priority of the World Health Organization for health improvement of the world population (Daar et al., 2002, Nat. Genet., 32:229-232). Severe blood infections are an important cause of morbidity and death in hospitalized patients worldwide and one of the most important challenges in critical care. For example, recent estimates of sepsis incidence are of 240 cases per 100 000 in the United States. The human and economic burden of sepsis is considerable (Grossi et al., 2006, Surg. Infect. (Larchmt), 7:S87-S91). Despite advances in infectious diseases and critical care management and numerous attempts to develop new treatments, sepsis mortality rate remains unacceptably high, ranging from 20% to 50%. Recognizing the signs of severe blood infections and/or severe sepsis and making an early and accurate diagnosis of it are the key to improving care and increasing the survival rate. Indeed, rapid diagnostics could increase patient survival by reducing the time interval between blood sampling and antimicrobial therapy application.

A need exists for efficient and accurate diagnostic tests for bodily fluid infections that would i) recover sufficient microbial cells for their detection, ii) recover microbial cells rapidly, iii) recover a large diversity of microbial species and iv) identify pathogens rapidly and accurately. The present invention seeks to meet these and other needs.

For several decades, different strategies have been used to try to meet such needs. The current standard is a broth-based blood culture system that favors growth of a majority of microorganisms present in a blood sample allowing them to multiply to a detectable level (Cockerill et al., 1996, J. Clin. Microbiol., 34:20-24; Murray et al., 1991, J. Clin. Microbiol., 29:901-905). However, such technique involves subsequent subculture on solid media for isolation and identification of microbial species. Consequently, several days are required to obtain an accurate diagnosis.

Saponins are naturally occurring surface-active glycosides having surfactant properties. They are mainly produced by plants but also by lower marine animals and some bacteria. They consist of a sugar moiety linked to a hydrophobic aglycone (sapogenin). The great complexity of saponin's structure arises from the variability of the aglycone structure, the nature of the side chains and the position of attachment of these moieties on the aglycone (Francis et al., 2002, British J of Nutrition, 88: 587-605). Saponins are known to interact with membranes of eukaryotic cells. Saponins are commonly used at 0.04%-0.2% concentrations to permeabilize plasma membranes. Such permeation may even lead to the destruction of the membrane with succeeding cell death. This process is function of the applied concentration and specific molecular structure of the saponin used (Melzig, et al. 2001, Planta Med., 67:43-48). It has been showed that the membrane binding site is cholesterol (Milgate et al. 1995, Nutrition Research, 15, no. 8; 1223-1249). Once bound to cholesterol, saponins induce changes in the membrane structure and permeability associated with disturbance of the ionic homeostasis between the intracellular and extracellular compartment. In yeast, molecules of ergosterol are found in the membrane instead of cholesterol. Studies showed that steroidal saponins (neutral saponins) preserve both hemolytic and antifungal activities, while triterpenoid saponins (acid saponins) show only hemolytic activity with no detectable antifungal activity. It is suggested that triterpenoid saponins may have a weaker affinity for ergosterol than cholesterol (Takechi et al. 2003, Phytother. Res., 17:83-85). Leconte et al. (Leconte et al. 1997, Phytochem., 44:575-579) demonstrated that cycloiridals, a class of triterpenoid from various Iris species, were able to stabilize yeast membranes after a disruption treatment by steroidal saponins. Triterpenoid saponins have been detected in many legumes such as soybeans, beans, peas and lucerne, as well as in alliums, tea, spinach, sugar beet, quinoa, liquorice, sunflower, horse chestnut and ginseng. One extensively studied group of triterpenoid saponins is produced from *Quillaja saponaria*, a tree native to the Andes region (Francis at al., 2002, British J of Nutrition, 88: 587-605). Saponins represent 20-25% of the extractable material from this source (Barr, et al., 1998, Ad Drug Deliv Rev, 32: 247-271). Commercially available saponin preparations may inhibit bacterial growth. Low molecular weight antibacterial contaminants may be removed from commercially available saponins by purification of the extracts by filtration (Dorn, G., Detoxification of saponins, U.S. Pat. No. 3,883,425, 1975).

Dorn et al. (U.S. Pat. No. 4,164,449) developed a method to lyse blood components with a minimum of 0.1 mg/mL and a maximum of 20 mg/mL of purified saponin. This method concentrates microbial cells by centrifugation and recovered cells are inoculated on an agar plate. A product based on this method is sold commercially as the Isostat®/Isolator™ (formerly named Isolator™ 10) and contains 1.83 mg/mL of purified saponin once mixed with the blood sample (Carter-Wallace, Inc., Cranbury, N.J. 08512-0181). This method allows detection of low-level bacteremia and fungemia caused by *Enterobacteriacae, Staphylococcus epidermidis* and yeasts within 1 to 2 days (McLaughlin et al. 1983, J. Clin. Microbiol., 18:1027-1031; Kiehn et al., 1983, J. Clin. Microbiol., 18:300-304). The increased sensitivity and shorter detection time may be due to the concentration of microbial cells from the initial blood sample volume. Another explanation for the improved detection obtained with Isolator™ 10 may be related to the release of intracellular microorganisms after lysis of some white blood cells by the saponin treatment. (Taylor, 1994, Eur. J. Clin. Microbiol. Infect. Dis., 13:249-252; Murray et al., 1991, J. Clin. Microbiol., 29:901-905). Some manufacturers of blood culture systems have supplemented their blood culture media with saponin (Murray et al., 1991, J. Clin. Microbiol., 29:901-905; Becton Dickinson BACTEC™ system; Hoffman La Roche biphasic Septi-Chek system).

Several groups compared blood culture media supplemented with saponin (varying from 0.03 mg/mL to 2 mg/mL of saponin when combined with a blood sample) or Isolator™

10 product (1.83 mg/mL of saponin when combined with a blood sample) to the standard blood culture media to detect microorganisms in septicemic patients. These references suggest that microorganisms detection in blood specimen cannot be based only on a method using saponin. Indeed, they showed that Isolator™ 10 was not efficient for detection of *Pseudomonas* species in low-level bacteremia (Kiehn et al., 1983, J. Clin. Microbiol., 18:300-304; Henry et al., 1983, J. Clin. Microbiol., 17:864-869; Murray at al., 1991, J. Clin. Microbiol., 29:901-905). Another group found similar limitations for the detection of anaerobic species (McLaughlin at al., 1983, J. Clin. Microbiol., 18:1027-1031).

Spears et al. (EPO Publication No. 0,745,849) reported the use of a saponin or Triton™ in saline solution for whole blood lysis. Their method aims to process blood specimens in order to remove inhibitors of subsequent nucleic acids analysis. In this method, the blood sample is lysed by the addition of saponin to about 0.2 to 0.5% (2 to 5 mg/mL).

Another method, without saponin, was used to concentrate microorganisms from the initial blood sample volume (Bernhardt at al., 1991, J. Clin. Microbiol., 29:422-425). Blood sample is centrifuged to form density gradient with Ficoll™-hypaque to separate red blood cells from white blood cells. The upper layer containing white blood cells is filtered through a 0.22 μm pore size filter to retain microbial cells on the filter membrane. The filter is then placed on top of an agar plate to allow microbial growth. With this method, all microorganisms were detected within 18 hours after filtration in comparison to 24-48 hours with standard culture. However, among the 12 bacterial species tested in spiked blood sample, only the *Pseudomonas aeruginosa* spiked sample allowed for the recovery of microorganisms equivalent to blood culture on agar plate.

In brief, actual methods of detection remain time-consuming mainly due to the use of microbial cell culture to detect isolated pathogens. Furthermore, blood culture systems (e.g. BACTEC™, Isostat®/Isolator™) all use non-heated aqueous saponin solutions.

Saponins' structure may undergo chemical transformations during storage or processing which in turn may modify their properties and activity. The use of heated saponin derivative in hematology has been reported (EPO Publication No. EP 1,422,509). This method aims at red blood cells lysis with saponin while quenching the lysis activity to preserve white blood cells for further analysis. This saponin derivative solution (50 mg/mL), heated at 121° C. for 30 minutes, was used in combination with an acid and/or surfactant to allow a broader range of saponin concentrations (0.02-0.035 mg/mL when combined with a blood sample). Furthermore, this patent describes a heating procedure that enhances the stability of the reagents over time. HPLC analysis indicated that this heating process led to an additional unidentified peak, which further appeared to have no lytic capability. It was suggested that the heating procedure removed unstable components from saponin that could degrade over time. It has been reported that saponins from intact soybeans are hydrolyzed into Group B and E saponins upon heating in alkaline solutions in the presence of iron (Güçlü-Üstündag, Ö. et al., 2007, Crit. Rev Food Sci Nut: 231-258). Moreover, the heating procedure has been shown to modify biological functions of soy saponins (Okubo, K., et al, Oxygen-Saponins used in food and agriculture, Plenum Press, NY, 1996).

In the majority of the above described reports, saponin solutions are filtered purified after dissolution using 0.8 to 0.2 μm filtering devices with various types of membranes and keeping the filtrate. The effect of filtration in each case may be complex to measure since variations in the ability of saponin from different sources to form micelles around cholesterol molecules may be due to differences in molecular structures contained (San Martin et al., 2000, J. Sci. Food Agric., 80:2063-2068). Since *Quillaja saponin* is a biological extract rather than a synthetic compound, commercial products may contain various impurities such as salts, or surface-active molecules which affect micelle-forming capabilities of saponin molecules (Mitra et al., 1997, J. Agric. Food Chem., 45:1587-1595). These concentrations are subject to vary since the dissolution of saponin crude extracts in water is difficult to achieve efficiently. *Quillaja* bark saponin is soluble in alcohol, ether, acetone, ethyl acetate and/or glacial acetic acid (Güçlü-Üstündag, Ö., et al., 2007, Crit. Rev Food Sci Nut: 231-258).

In U.S. Pat. No. 3,883,425, an aqueous saponin solution is prepared by keeping the residue retained by the filtration device instead of the filtrate. This patent describes a procedure aiming at removing constituents in the saponin extract that have a molecular weight of less than about 600, described as being toxic to microbial organisms. During filtration, these toxic molecules pass through the membrane and remain in the filtrate.

Recent advances in molecular biology have allowed the development of tools for sensitive and accurate identification of bloodstream pathogens by bypassing microbial culture steps. Progress in nucleic acid amplification technologies allowed advances in the detection of small amounts of nucleic acids. However, new challenges are associated with these technologies. A first challenge involves a need for the recovery of most microbial cells from a sample to detect microbial nucleic acids by amplification without any cell replication step, even when blood samples contain less than 10 CFU/mL. A second challenge involves the need for decrement of human genomic DNA/microbial genomic DNA ratios to favor microbial DNA amplification. A third challenge involves the need to control nucleic acid amplification inhibitors originating from blood (e.g. inhibitors of polymerase chain reaction (PCR). The present invention seeks to meet these and other needs. PCR is by far the most popular nucleic acid amplification technology. PCR-based diagnosis of microbial infections and genetic diseases may be reduced or blocked by the presence of PCR-inhibitory substances in blood samples (Hoorfar et al., 2004, J. Appl. Microbiol., 96:221-222). PCR inhibitors have been identified as mainly heme and leukocyte DNA, but also anticoagulants like EDTA and heparin. More recently, Immunoglobulin G in human plasma, hemoglobin and lactoferrin in erythrocytes and leukocytes respectively, also proved to be major inhibitors of diagnostic PCR from blood (Al-Soud et al., 2000, J. Clin. Microbiol., 39:485-493). A need exists for improving isolation of microorganism from blood specimen that may be applicable for detection of both bacteria and fungi.

Among published and commercially available products, some methods involve a total simultaneous lysis of red and white blood cells as well as microbial cells to purify total nucleic acids afterwards (Jordan et al, 2005, J. Mol. Diagn., 7:575-581; NucliSens® easyMAG™ system from BioMérieux; SeptiFast prep kit from Roche Diagnostics; and Isoquick® nucleic acid extraction kit from ISC BioExpress). A disadvantage of this strategy is the presence of large amounts of blood cells nucleic acids as compared to microbial cells nucleic acids. This may prevent a good analytical sensitivity of microbial nucleic acids detection.

Other methods proceed to lysis of blood and microbial cells in separate steps followed by purification of nucleic acids. With this strategy, some groups use a hypotonic shock to lyse red blood cells and a combination of 0.2% SDSproteinase K to lyse white blood cells before lysing yeast cells with an enzymatic digestion (White et al., 2006, Clin. Infect. Dis., 42:479-486; Loeffler et al., 2002, J. Clin. Microbiol., 40:2240-2243). Another group uses the Isolator™ 10 technology to lyse blood cells. The harvested yeast cells mixed with blood cells residues are then enzymatically digested and nucleic acids are purified (U.S. Pat. No. 5,645,992). These methods were developed to only detect fungal species.

The MolYsis Basic5 kit from Molzym uses guanidium thiocyanate and a chaotropic-resistant DNase to lyse blood cells and remove their nucleic acids prior to bacterial cell lysis and nucleic acid extraction. Bougnoux et al. (Bougnoux et al., 1999, J. Clin. Microbiol., 37:925-930) use a combination of sucrose and Triton™ X-100 to treat blood samples spiked with *Candida* cells to lyse blood cells. After centrifugation of unlysed cells, the pellet is resuspended and digested with DNaseI to degrade nucleic acids released from white blood cells. After digestion, the cell suspension including the spiked *Candida* cells is centrifuged. The supernatant is discarded and the pellet is resuspended and submitted to a lyticase treatment to digest the yeast cell walls prior to their nucleic acid extraction.

The SeptiFast prep kit (LightCycler® SeptiFast Test $M^{GRADE}$) was developed for the detection of both bacteria (19 different groups and 25 different species) and fungi (6 different species). The analytical sensitivity of this test is approximately 30 CFU of microbe/mL of blood. This system requires numerous handling steps and takes about 2 hours of handling prior to the extraction of human and microbial genomic DNA. Furthermore, it was shown that a majority of blood samples collected from septicemic patients may contain as low as 10 colony-forming units (CFU) of microbes per mL of blood (Jonsson et al., 1993, APMIS, 101:595-601).

In addition to nucleic acid-based methods, detection and/or identification of microbes may be performed by detecting phenotypical characteristics, microbial antigens, cellular components and/or physiological activities of microbial cells. Multiparametric analysis of microbial markers is useful for identifying microbes, for example, using microanalytical methods and microfabricated devices (Link et al., 2007, Nat. Rev. Microbiol. 5:680-688; Weibel et al., 2007, Nat. Rev. Microbiol. 5:209-218). Viable microbial cells (and/or metabolically active microbes) may be required to perform such analysis (Metzger, S. et al, ASM general meeting 2008, Abstract C-145; Metzger, S. et al, ASM general meeting 2008, Abstract C-005)

The present description refers to a number of documents, the content of which is herein incorporated by reference in their entirety.

SUMMARY OF THE INVENTION

In the present invention, a new and rapid (around 30 minutes) method for isolating and/or detecting microorganisms and microorganisms nucleic acids from bodily fluids has been developed. The method(s) of the present invention may comprise (may consist in) the steps of lysing bodily fluid (host) cells while protecting (preserving) microbial cells and their nucleic acids using a solution which may comprise treated saponin at a final concentration ranging from about 20 to about 100 mg/mL; washing bodily fluid cell lysate to remove a significant fraction of nucleic acids from bodily fluid host cells as well as controlling inhibitors from bodily fluid components while preserving microbial cells and their nucleic acids; harvesting concentrated microbial cells and their nucleic acids and/or extracting microbial nucleic acids. This invention leads to a simple method achieving from about 80- to 500-fold increase in the concentration of microbial cells from the original sample. The concentration and enrichment protocol of this invention is efficient for extracting microbial nucleic acids from bodily fluids with high as well as with low microbial loads and is suitable for a broad spectrum of microorganisms. This protocol is also efficient for obtaining viable and/or metabolically active microbial cells.

In one aspect thereof, the present invention relates to a method for isolating microorganisms and/or microorganisms nucleic acids from a bodily fluid that may comprise or may be suspected to comprise microorganisms and/or host cells and/or host cells debris. The method may comprise, for example, contacting the bodily fluid with a saponin formulation and/or obtaining isolated microorganisms and/or microorganisms nucleic acids by removing host cells and/or host cell debris. Microorganisms nucleic acids may further be isolated by lysing the isolated microorganisms.

In a second aspect thereof, the present invention relates to a method for detecting microorganisms in a bodily fluid. The method may comprise, for example, amplifying microorganisms nucleic acids obtained from the method of isolation of the present invention. The method may further comprise detecting amplified microorganisms nucleic acids by hybridizing a probe and/or a collection of probes selected from those capable of specific binding to amplified nucleic acids of at least one microorganism. The method may also comprise, for example, analyzing the antigenic expression, cellular activity and/or physiological activity of microorganisms obtained from the method of isolation of the present invention.

In a third aspect thereof, the present invention relates to assays that may be based on methods of isolation and/or methods of detection of the present invention.

In a fourth aspect thereof, the present invention relates to a kit for isolating microorganisms and/or microorganisms nucleic acids from a bodily fluid that may comprised or may be suspected of comprising microorganisms and/or host cells and/or host cell debris. The kit may comprise a vessel containing a saponin formulation. The kit may further comprise a vessel containing detection means. The present invention also relates to the use of kits for isolating and/or detecting microorganisms and/or microorganisms nucleic acids.

In a fifth aspect thereof, the present invention relates to a method for diagnosing a bodily fluid infection in a subject in need thereof. The method may comprise detecting microorganisms wherein the detection may be indicative of an infection associated with the microorganisms detected.

In a sixth aspect thereof, the present invention relates to a saponin formulation prepared by heating, filtering and/or autoclaving. The present invention also relates to the use of such saponin formulation for the isolation of microorganisms and/or microorganisms nucleic acids from a bodily fluid that may comprise or may be suspected to comprise microorganisms and/or host cells and/or host cells debris.

BRIEF DESCRIPTION OF THE DRAWINGS

In drawings which illustrates non-limitative exemplary embodiments of the present invention.

DETAILED DESCRIPTION

Figure 1:
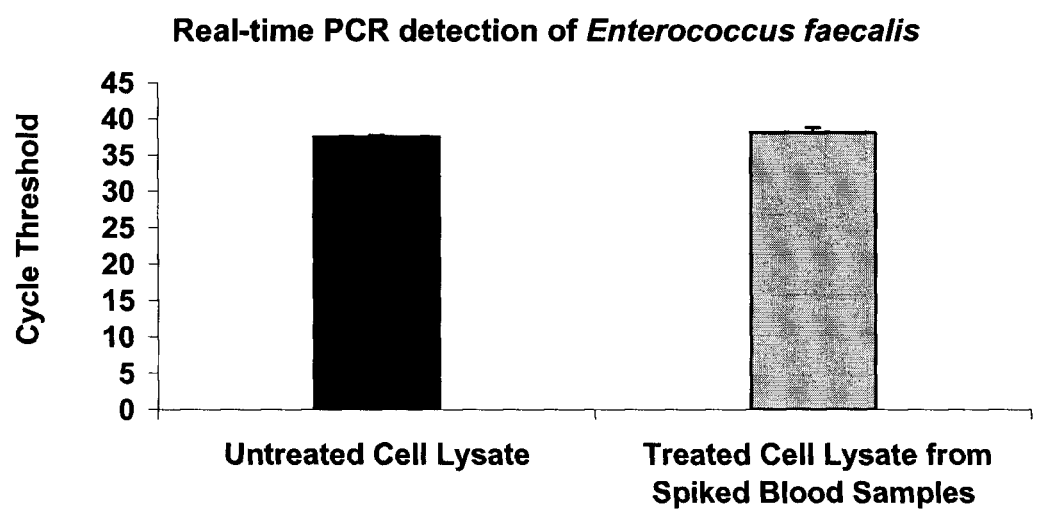
FIG. 1 shows the efficient recovery of microbial cells and their nucleic acids from blood samples spiked with 10 CFU/ml of *Enterococcus faecalis*. The detection of microbial nucleic acids by real-time PCR from the spiked blood sample treated with the method of this invention was compared with a control cell lysate prepared directly from 50 CFU of untreated bacteria. Standard deviation for the spiked blood samples is from five blood donors with a minimum of ten replicates per donor while the standard deviation for the control is for a single replicate for each of the five donors.

In order to provide a clear and consistent understanding of the terms used in the present disclosure, a number of definitions are provided below. Moreover, unless defined otherwise, all technical and scientific terms as used herein have the same meaning as commonly understood to one of ordinary skill in the art to which this invention pertains.

As used in the specification and claim(s), the term "about" is used to indicate that a value includes an inherent variation of error for the device and/or the method being employed to determine the value. Where a value is explicitly recited, it is to be understood that values which are about the same quantity or amount as the recited value are also within the scope of the invention, as are ranges based thereon. Use of the singular forms "a," "an," and "the" include plural references unless the context clearly dictates otherwise.

In one aspect thereof, the present invention relates to a method for isolating (concentrating) microorganisms (viable and/or metabolically active microorganims) and/or microorganisms nucleic acids (for example and without limitation, DNA) from a bodily fluid that may comprise or may be suspected to comprise microorganisms and/or host cells and/or host cells debris. The method may comprise (may consist of), for example, contacting the bodily fluid with a saponin formulation and/or obtaining isolated microorganisms and/or microorganisms nucleic acids by removing host cells and/or host cell debris. Microorganisms nucleic acids may further be isolated by lysing the isolated microorganisms.

A saponin formulation may be prepared by resuspending saponins into a suitable hypotonic and/or physiological solution. Plant-derived saponins from *Quillaja saponaria* Molina bark cleared out from low molecular weight contaminants is an exemplary saponin source. Exemplary hypotonic or physiological solutions include, but are not limited to, water, low ionic strength buffers such as TE (10 mM Tris, 1 mM EDTA, pH 8), phosphate buffer, phosphate buffer saline (PBS 1×:137 mM NaCl, 10 mM Phosphate, 2.7 mM KCl, and a pH of 7.4), ethanol and/or acidified solutions. An exemplary hypotonic diluent of the present invention may be TE 1× to 2×. An exemplary physiological diluent of the present invention may be PBS 1×. A saponin suspension may be at a concentration of from about 100 to about 133 mg/mL in hypotonic and/or physiological diluent.

A saponin formulation of the present invention may be autoclaved, filtered and/or heated prior to filtration. For example, heating saponin at around 95° C. may, for example, increase dissolution. Saponin may be filtered, for example on a paper filter (including for example a No. 5 paper filter from Whatman™) which may remove larger undissolved particulate material. The saponin may also be filtered with a 5 μm membrane and/or with a 0.2 μm membrane that may remove finer particulate material. In an exemplary embodiment of the present invention, saponin may be filtered using a 5 μm cellulose nitrate membrane and/or with a 0.2 μm polyethersulfone membrane.

In an exemplary embodiment of the present invention, saponin is filtered and autoclaved. Such treatment results in a saponin formulation that may be referred to as filtered/autoclaved-treated saponin (FATS) solution. In another exemplary embodiment saponin is heated, filtered and autoclaved. Such treatment results in a saponin formulation that may be referred to as heated/filtered/autoclaved-treated saponin (HFATS) solution. FATS and/or HFATS formulation may be used in the present invention. HFATS formulation may advantageously be used in the present invention.

The final concentration of saponin may be above 20 mg/mL, above 25 mg/mL, above 40 mg/mL, above 50 mg/mL, above 75 mg/mL and/or may be above 80 mg/mL. The final concentration of saponin may be from 20 mg/mL to 100 mg/mL. For example, the final concentration of saponin may be from 25 mg/mL to 100 mg/mL, 30 mg/mL to 100 mg/mL, 40 mg/mL to 100 mg/mL, 60 mg/mL to 100 mg/mL, 75 mg/mL to 100 mg/mL. The final concentration of saponin may be from 40 mg/mL to 50 mg/mL. As used herein, "final concentration" in respect to saponin relates to the saponin concentration once mixed with a sample, for example, when mixed (or contacted with) a bodily fluid. It is to be understood that any specified range or group is as a shorthand way of referring to each and every member of a range or group individually as well as each and every possible sub-ranges or sub-groups encompassed therein and similarly with respect to any sub-ranges or sub-groups therein. The present invention relates to and explicitly incorporates each and every specific member and combination of sub-ranges or sub-groups therein whatsoever. Thus, for example, when it is said that a final concentration of saponin may be above 75 mg/mL, the final concentration of saponin may be 75.5 mg/mL, 76 mg/mL, 77 mg/mL, 78 mg/mL, 100 mg/mL, 150 mg/mL, etc. In another example, when it is said that a final concentration of saponin may be between 75 mg/mL and 100 mg/mL, the final concentration of saponin may be 75, 76, 77, 78, 79, 80, 81, 82, 83, 84, 85, 86, 87, 88, 89, 90, 91, 92, 93, 94, 95, 96, 97, 98, 99 or 100 mg/mL and/or any value therebetween.

The term "saponin" is meant to comprise steroidal saponin, triterpenoid saponin and/or combination thereof. In an exemplary embodiment of the present invention, saponin is triterpenoid saponin.

The saponin formulation of the present invention may be compatible with nucleic acid amplification. The saponin formulation of the present invention may selectively lead to the lysis of bodily fluid host cells in a bodily fluid that may comprise and/or may be suspected to comprise microorganisms and/or host cells while preserving the integrity and/or viability of the microorganisms.

As used herein, a "bodily fluid" may be amniotic fluid, aqueous humour, bile, bladder lavage, blood, breast exudate, bronchioalveolor lavage, cerebrospinal fluid, chyle, chyme, cytosol, feces (in semi-fluid or fluid form), interstitial fluid, lymph, menses, mucus, plasma, pleural fluid, pus, saliva, sebum, semen, serum, sputum, sweat, synovial fluid, tears, urine and/or vitreous humour. In an exemplary embodiment of the present invention, the bodily fluid may be blood. In another embodiment, the bodily fluid (sample) may be obtained from a mammal such as a human being.

The bodily fluid may be contacted at least once with the saponin formulation. In an exemplary embodiment of the present invention, the bodily fluid may be contacted once with the saponin formulation (one-step method). In another exemplary embodiment of the present invention, the bodily fluid may be contacted twice with the saponin formulation (two-step method). The contact of the saponin formulation with the bodily fluid may result in more than 80%, more than 85% and/or more than 90% bodily fluid host cells lysis.

Microorganisms of the present invention may be bacteria, yeast, fungi and/or combination thereof. The microorganisms of the present invention may be aerobic and/or anaerobic. The terms "microorganisms", "microbial cells" and "microbes" may be used interchangeably in the current text. In an exemplary embodiment, microorganisms may cause bodily fluid infections such as bloodstream infections. Microorganisms of the present invention may also be sepsis-causing microorganisms, that is, microorganisms such as bacteria, yeast, and/or fungi that lead to a systemic inflammatory response syndrome (SIRS).

Microorganisms of the present invention include, but are not limited to, the *Acinetobacter* genus, *Bacteroides* genus, *Burkholderia* genus, *Capnocytophaga* genus, *Clostridium* genus, *Corynebacterium* genus, *Citrobacter* genus, *Enterobacter* genus, *Enterococcus* genus, *Escherichia* genus, *Haemophilus* genus, *Klebsiella* genus, *Proteus* genus, *Pseudomonas* genus, *Serratia* genus, *Staphylococcus* genus, *Stenotrophomonas* genus, *Streptococcus* genus, *Aspergillus* genus and/or *Candida* genus.

Exemplary microorganisms may be *Acinetobacter baumannii, Bacteroides fragilis, Burkholderia cepacia, Capnocytophaga canimorsus, Clostridium perfringens, Corynebacterium jeikeium, Citrobacter freundii, Citrobacter koseri, Enterobacter aerogenes, Enterobacter cloacae, Enterococcus faecalis, Enterococcus faecium, Escherichia coli, Haemophilus influenzae, Klebsiella oxytoca, Klebsiella pneumoniae, Proteus mirabilis, Pseudomonas aeruginosa, Serratia marcescens, Staphylococcus aureus, Staphylococcus epidermidis, Staphylococcus haemolyticus, Staphylococcus hominis, Staphylococcus warneri, Stenotrophomonas maltophilia, Streptococcus agalactiae, Streptococcus anginosus, Streptococcus dysgalactiae, Streptococcus mutans, Streptococcus pneumoniae, Streptococcus pyogenes, Streptococcus sanguinis, Aspergillus fumigatus, Aspergillus flavus, Aspergillus terreus, Candida albicans, Candida glabrata, Candida krusei, Candida parapsilosis* and/or *Candida tropicalis*.

In an exemplary embodiment, the isolated microorganisms obtained by the method of the present invention may be viable and/or are metabolically active. "Viable microorganisms" are microorganisms that may be able to undergo cell division. "Metabolically active microorganisms" are microorganisms that may carry metabolic functions but that may not be able to undergo cellular division.

Isolation of microorganisms and microorganisms nucleic acids according to the method of the present invention may result in 80- to 500-fold concentration of the microorganisms and microorganisms nucleic acids from the bodily fluid. Microorganisms may be present at low and/or high concentration in a bodily fluid. Typically, microorganisms concentrations in bodily fluids may be measured by CFU counts which express the number of viable microbial cells per milliliter. An exemplary low microorganisms concentration in bodily fluid may be 10 CFU/mL or less. For example and without limitation, a low microorganisms concentration may be, 0.1 to 10 CFU/ml and any range in between or even less. An exemplary high microorganisms concentration in bodily fluid may be from 100-10,000 CFU/mL or more.

The method of the present invention may have an analytical sensitivity of about 50 CFU/mL, about 40 CFU/mL, about 30 CFU/mL, about 25 CFU/mL and/or less. For example, the analytical sensitivity may be from about 1 to about 50 CFU/mL and/or from about 1 to about 25 CFU/mL.

According to the present invention, isolated microorganisms and/or microorganisms nucleic acids may be substantially free of amplification and/or detection inhibitors. According to the present invention, "amplification inhibitors" may be any substance that impedes and/or prevents amplification of a target sequence.

According to the present invention, host cells may be any endogenous cells in a given host, for example a mammal such as a human. Host cells (endogenous cells) may be present in a bodily fluid sample. Exemplary host cells of a bodily fluid may be red and white blood cells.

Removing host cells and/or host cell debris may involve washing the bodily fluid (sample) by concentrating insoluble material and resuspending this insoluble material in a suitable washing solution. Washing steps of concentrating and resuspending insoluble material may be repeated a number of times, for example, to maximize removal of nucleic acid amplification/detection methods inhibitors. Concentration methods may include, without limitation, centrifugation, filtration, surface binding and/or magnetic trapping, etc. Exemplary suitable washing solutions may include, without limitation, water, buffers such as TE, phosphate buffer, Tris buffer, phosphate-buffered saline, Tris-buffered saline, ethanol-containing aqueous solutions and/or acidified solutions, etc.

Isolated microorganisms may be lysed (for example by chemical, enzymatic and/or mechanical lysis) to extract and/or purify their nucleic acids by any means known by a person skilled in the art. An exemplary nucleic acid extraction method may be the BD GeneOhm™ Lysis Kit (BD Diagnostics-GeneOhm).

In a second aspect thereof, the present invention relates to a method for detecting microorganisms in a bodily fluid. The detection method may comprise (may consist), for example, amplifying microorganisms nucleic acids obtained from the method of isolation of the present invention. The method may further comprise detecting amplified microorganisms nucleic acids. The method may further comprise, for example, analyzing the phenotypic, antigenic expression, cellular activity and/or physiological activity of microorganisms obtained from the method of isolation of the present invention. Phenotypic, antigenic expression, cellular and/or physiological analyses of microbial cells may be performed by any mean known by a person skilled in the art.

According to the present invention, "amplification" means an increase in number of a particular nucleic acid sequence and may be accomplished by a number of in vitro nucleic acid amplification techniques known in the art. Amplification techniques may include methods requiring temperature cycling (such as PCR, ligase chain reaction, transcription based amplification) and/or isothermal amplification systems (such as self-sustaining sequence replication, replicase system, helicase system, strand displacement amplification, rolling circle-based amplification and NASBA). According to an exemplary embodiment of the present invention, amplification of microorganisms nucleic acids may be performed by polymerase chain reaction and/or any variations thereof, including, without limitation, allele-specific PCR, asymmetric PCR, hot-start PCR, intersequence-specific PCR, methylation-specific PCR, miniprimer PCR, multiplex ligation-dependent probe amplification, multiplex-PCR, nested PCR, quantitative PCR, reverse transcription PCR and/or touchdown PCR. Amplification may be performed using primers and/or a collection of primers that may be selected from those capable of specific binding to nucleic acids of at least one microorganism. Amplified microorganisms nucleic acids may be detected by hybridizing a probe and/or a collection of probes capable of specific binding to amplified nucleic acids of at least one microorganism. Exemplary primers and probes used in the present invention may be SEQ ID NO.: 1 to 32.

In a third aspect thereof, the present invention relates to assays that may be based on methods of isolation and/or methods of detection of the present invention.

In a fourth aspect thereof, the present invention relates to a kit for isolating microorganisms and/or microorganisms nucleic acids from a bodily fluid that may comprise or may be suspected of comprising microorganisms and/or host cells and/or host cell debris. The kit may comprise a vessel containing a saponin formulation of the present invention and/or a vessel containing detection means. The present invention also relates to the use of kits of the present invention for isolating and/or detecting microorganisms and/or microorganisms nucleic acids. A kit of the present invention may also comprise instructions for its use.

According to the present invention, detection means may consist, for example, in primers capable of specific binding to nucleic acids of at least one microorganism, probes capable of specific binding to nucleic acids of at least one microorganism, phenotype analysis detection means, antigenic expression analysis detection means, cellular activity detections means and/or physiological activity detections means.

In a fifth aspect thereof, the present invention relates to a method for diagnosing a bodily fluid infection in a subject in need thereof. The method may comprise detecting microorganisms wherein the detection may be indicative of an infection associated with the microorganisms detected. As used herein, a subject in need thereof may be a subject having, suspected of having or at risk of having a bodily fluid infection. In an exemplary embodiment of the invention, a subject is a mammal such as a human being.

In a sixth aspect thereof, the present invention relates to a saponin formulation prepared by heating, filtering and/or autoclaving. The present invention also relates to the use of such saponin formulation for the isolation of microorganisms and/or microorganisms nucleic acids from a bodily fluid that may comprise or may be suspected to comprise microorganisms and/or host cells and/or host cells debris.

The saponin formulation of the present invention may be used at a final concentration of from 20 mg/mL to 100 mg/mL. The saponin formulation may be used at a final concentration of more than 75 mg/mL.

The present invention also relates to a method for concentrating and/or detecting microorganisms and microorganisms nucleic acids from a bodily fluid that may comprise and/or may be suspected to comprise microorganisms and/or host cells. The method may comprise the step of a. lysing host cells using a saponin formulation, b. separating the microorganisms from the lysed host cells, c. washing the separated microorganisms and/or d. harvesting the microorganisms. The method may further comprise the steps of e. extracting nucleic acids from the microorganisms and/or f. detecting the microorganisms and/or the microorganisms nucleic acids.

Further scope and applicability of the present invention will become apparent from the detailed description given hereinafter. It should be understood, however, that this detailed description, while indicating exemplary embodiments of the invention, is given by way of example only, since various changes and modifications will become apparent to those skilled in the art.

EXAMPLES

Example 1

Experimental Procedures

The method(s) of the present invention comprises the steps of lysing blood cells (for example, more than 90% of blood cells) while protecting microbial cells and their nucleic acids using a solution which may comprise treated saponin at a final concentration ranging from about 20 to about 100 mg/mL; washing blood cell lysate to remove a significant fraction of nucleic acids from blood cells as well as controlling inhibitors from blood components while preserving microbial cells and their nucleic acids; harvesting concentrated microbial cells and their nucleic acids and/or extracting microbial nucleic acids. For such purpose, the following conditions and/or reagents are used.

Saponin Reagent Preparation

Saponin reagent was prepared by resuspending saponins in the form of powdered extract from *Quillaja saponaria* Molina bark into a suitable hypotonic or a physiological solution. Saponin extracts from *Quillaja saponaria* bark, cleared out from low molecular weight contaminants, was from Sigma-Aldrich (Catalog No. S4521). Saponin is prepared by dissolving 100 to 133 mg of powder per mL of TE buffer diluent or PBS.

"FATS" Saponin Formulation Preparation Steps
1) Saponin powder is mixed with TE 1× or PBS 1×;
2) the saponin is dissolved by mixing at room temperature for several hours;
3) the saponin solution is sequentially filtered through a No. 5 paper filter (Whatman™) a 5 µm cellulose nitrate membrane filter (Whatman™) and a 0.2 µm polyethersulfone membrane filter (Nalgene); and
4) the filtered solution is autoclaved at 121° C. during 30 minutes and stored at 4° C.

"HFATS" Saponin Formulation Preparation Steps
1) Saponin powder is mixed with TE 1× or PBS 1×;
2) the saponin solution is heated at 95-100° C. with agitation until complete dissolution;
3) the warm saponin solution is sequentially filtered through a No. 5 paper filter (Whatman™), a 5 µm cellulose nitrate membrane filter (Whatman™) and a 0.2 µm polyethersulfone membrane filter (Nalgene); and
4) the filtered solution is autoclaved at 121° C. during 30 minutes and stored at 4° C.

Whenever possible, to minimize nucleic acid contamination levels from reagents and solutions, stock solutions were filtered on 0.1 µm polyethersulfone membranes (Pall). In addition to 0.1 µm filtration, water, TE, PBS and other heat stable solutions were autoclaved.

Blood Cell Lysis Conditions

Two-Step Method

The first FATS or HFATS treatment is performed by adding the equivalent of about 3 blood volumes of FATS or HFATS at 100 mg/mL with a blood sample for a final FATS or HFATS concentration of 75 mg/mL. The blood sample is mixed with FATS or HFATS for 10 seconds using a vortex set at maximum speed. This first FATS or HFATS treatment is followed by centrifugation at 10 000 g for 5 minutes. The supernatant is discarded and the pellet is resuspended with the equivalent of about 2 initial blood volumes of FATS or HFATS at 100 mg/mL. For this second treatment, the final FATS or HFATS concentration is 100 mg/mL. The blood sample is mixed with FATS or HFATS for 10 seconds using a vortex set at maximum speed. This second FATS or HFATS treatment is followed by centrifugation at 10 000 g for 5 minutes. The supernatant is discarded and the pellet is washed as described below.

One-Step Method

An alternative method is to treat a blood sample using a single treatment with FATS or HFATS. The blood sample is mixed directly with about 4 to 5 blood volumes of FATS or HFATS at 100 mg/mL to lyse red and white blood cells for a final FATS or HFATS concentration equivalent to 80-83.3 mg/mL. This HFATS treatment is followed by centrifugation at 10 000 g for 5 minutes. The supernatant is discarded and the pellet is washed as described in the next paragraph.

Pellet Washes

Examples of suitable rinsing and harvesting solutions may include, without limitation, water, buffers such as TE, phosphate buffer, Tris buffer, phosphate-buffered saline, Tris-buffered saline, ethanol-containing aqueous solutions and/or acidified solutions, etc. Rinsing and harvesting microbial cells and their nucleic acids may be achieved by vigorous agitation of the rinsing/harvesting solution with the pellet resulting from the previous steps. Exemplary rinsing/harvesting solution may be TE 1× buffer or PBS 1× buffer. The washes are accomplished by mechanically disrupting the pellet with up and down pipetting, followed by mixing for 10 seconds using a vortex set at maximum speed. Subsequently, the solution was centrifuged at 10 000 g for 1 minute, and the supernatant was discarded. The pellet may be washed once or more, for example, the pellet may be washed twice.

Harvesting Step

The washed pellet contains microbial cells and their nucleic acids (it may also contain blood cell residues). To harvest microbial cells and their nucleic acids, the washed pellet is vigorously shaken in a suitable rinsing/harvesting solution such as TE 1× for 15 seconds using a vortex set at maximum speed. The TE 1× volume represents 0.002-0.012× the initial blood volume. 80- to 500-fold concentration of starting microbial cells and their nucleic acids is thereby achieved.

The final undisrupted pellet is mechanically removed from the tube by mechanical separation using a micropipette tip. The remaining microbial cells and nucleic acids suspension is then ready for nucleic acid extraction. The rinsed pellet may also be further processed to obtain microbial cells. The rinsing and harvesting solution freed from the pellet may be further processed to extract microbial nucleic acids. The rinsing and harvesting solution freed from pellet may also be further processed to obtain microbial cells. At any step after blood cell lysis by HFATS and/or FATS solution, a sample of microbial cells and nucleic acid suspensions may be used for phenotypic, antigenic expression, cellular and/or physiological analyses.

As estimated by fluorescence activated cell sorter (EPICS XL, Beckman Coulter), lysis of over 90% of red and white blood cells can be achieved using one-step method with HFATS.

A person skilled in the art knows fluid displacement means as well as other ways to achieve separation and harvesting of soluble and insoluble fractions. Therefore, alternative means, ways, and devices designed to move fluids, and/or separate and/or recuperate soluble and insoluble fractions whether they are manual or automated, are within the scope of this invention.

Control of PCR Inhibitors

Potential PCR inhibitors present in DNA extracts can be monitored by adding a control amount of DNA target to the PCR mixture. This control may be performed in the same reaction tube or in parallel (Hoorfar et al., 2004, Lett. Appl. Microbiol., 38:79-80).

Example 2

Efficient Isolation and Detection of Microbial Cells and Their Nucleic Acids from Blood Samples 5 mL of whole blood samples were inoculated with an average of 10 CFU/mL of *Enterococcus faecalis*. The spiked blood was treated with saponin using the two-step method described in Example 1. During the first step, 15 mL of 100 mg/mL HFATS in TE 1× was added to the spiked blood sample and mixed for 10 seconds using a vortex set at maximum speed. Pelleted blood residues and microbial cells were obtained by centrifugation at 10 000 g for 5 minutes, and the supernatant was discarded. In a second step, 10 mL of 100 mg/mL HFATS in TE 1× was added to the harvested pellet and mixed 10 seconds using a vortex set at maximum speed, then centrifuged at 10 000 g for 5 minutes and the supernatant was discarded.

The pellet was washed in 1.7 mL of PBS 1× by up and down pipetting. The suspension was centrifuged at 10 000 g for 1 minute and the supernatant was discarded. The washing step was repeated once. 50 µL of TE 1× was added to the washed pellet. The washed pellet and TE 1× were vigorously agitated for 15 seconds using a vortex set at maximum speed. The pellet was removed by using a micropipette tip and the aqueous phase was transferred into a tube containing glass beads for microbial cell lysis using the BD GeneOhm™ Lysis kit.

*E. faecalis* nucleic acids were detected with a PCR assay developed using the rapid DNA amplification apparatus SmartCycler™ (Cepheid). This assay incorporates primers specific to *E. faecalis* tuf gene sequences (5'-ACTTGTC-CACGTTSGATRTCT-3', SEQ ID NO.: 1 and 5'-AAT-TAATGGCTGCWGTTGAYGAA-3', SEQ ID NO.: 2) and detects the generated amplicons with a TaqMan probe specific to the *E. faecalis* tuf gene (5'-ATCCCAACTCCA-GAACGTGAYA-3', SEQ ID NO.: 3). PCR reactions were preformed using 1×PCR reaction buffer (Promega) (1× buffer is 10 mM Tris-HCl at pH 9.1, 50 mM KCl, 3.3 mg/mL BSA, 0.1% Triton™ X-100 and 2.5 mM $MgCl_2$), 0.4 µM of each primer, 0.1 µM of the TaqMan probe, 0.2 mM each of the four dinucleotide triphosphate mix (GE Healthcare) and 0.025 U/µL of Taq DNA polymerase (Promega), coupled with the TaqStart® antibody (Clontech Laboratories). PCR cycling conditions using a SmartCycler™ (Cepheid) were as follows: 3 min at 95° C. for the initial denaturation, and then, 45 cycles of 10 sec at 95° C. for denaturation, 30 sec at 58° C. for annealing and 30 sec at 72° C. for extension.

The detection of microbial nucleic acids by real-time PCR from spiked blood sample treated with the method of this invention was compared with a control microbial cell lysate prepared directly from 50 CFU of untreated bacteria suspended in TE 1×, using the BD GeneOhm™ Lysis Kit (FIG. 1). Initial CFU/ml counts were determined by culturing serial dilutions in PBS 1× and plating on solid media. Correspondence between CFU and genome copy equivalent was confirmed using a standard curve with dilutions of purified *E. faecalis* genomic DNA. Plate counts confirmed that a range of 8 to 12 CFU/ml was tested for these assays, corresponding to 2 to 3 CFU per PCR reaction. Results showed that analogous cycle threshold values were obtained for both the control untreated cell lysate and the spiked blood sample thereby indicating that the method of the present invention is highly efficient for the recovery of microbial cells and their nucleic acids.

Example 3

Effect of Increasing Concentrations of Saponin on E. Coli Nucleic Acids Detection The effect of increasing concentrations of filtered, autoclaved treated saponin (FATS) solution on the detection of *E.* coli nucleic acids was monitored. The microorganism DNA was recovered from blood specimens spiked with live microbial cells. 10 mL of whole blood sample were inoculated with an average of 400 CFU of *E. coli* per mL. Initial CFU/ml counts were determined by culturing serial dilutions in PBS 1× on solid media. This assay was completed using the two-step treatment with FATS as described in Example 1. During the first step, 40 mL of FATS in TE 1× were added to the spiked blood sample and mixed for 10 seconds using a vortex set at maximum speed. A pellet was obtained by centrifugation at 10 000 g for 5 minutes, and the supernatant was discarded. In a second step, 45 mL of FATS in TE 1× was added to the pellet and mixed for 10 seconds using the vortex set at maximum speed. Subsequently, the solution was centrifuged at 10 000 g for 5 minutes, and the supernatant was discarded. The pellet was washed once in 500 µL of TE 1× by pipetting up and down. The suspension was then centrifuged at 10 000 g for 5 minutes, and the supernatant was discarded. Microbial cells and their nucleic acids in the washed pellet were resuspended in 20 µL of TE 5×. Mechanical lysis of the microbial cells and extraction of their nucleic acids was achieved by using the BD GeneOhm™ Lysis Kit (BD Diagnostics-GeneOhm). The resulting lysate containing microbial nucleic acids was quickly spun down and heated at 95° C. for 2 minutes as instructed by the manufacturer. In the same way, 5 mL of whole blood sample inoculated with 35 CFU of *E. coli* per mL were treated with 20 mL of HFATS using the one-step method.

*E. coli* nucleic acids were detected with a PCR assay developed using the rapid DNA amplification apparatus SmartCycler™ (Cepheid). This assay incorporates primers specific to *E. coli* tuf gene sequences (5'-TGGGAAGCGAAAATC-CTG-3', SEQ ID NO.: 4 and 5'-CAGTACAGGTAGACT-TCTG-3', SEQ ID NO.: 5) and detects the generated amplicons with a TaqMan probe specific to *E. coli* tuf gene (5'-AACTGGCTGGCTTCCTGG-3', SEQ ID NO.: 6). PCR reactions were performed in a 25 µL mixture containing 13 µL of lysate comprising the concentrated nucleic acids from microbial cells, 1×PCR reaction buffer (Promega) (1× buffer is 10 mM Tris-HCl at pH 9.1, 50 mM KCl, 3.3 mg/mL BSA, 0.1% Triton™ X-100 and 2.5 mM $MgCl_2$), 0.4 µM of each primer, 0.1 µM of the TaqMan probe, 0.2 mM each of the four dinucleotide triphosphate mix (GE Healthcare) and 0.025 U/µL of Taq DNA polymerase (Promega), coupled with the TaqStart® antibody (Clontech Laboratories). PCR cycling conditions were as follows: 2 min at 95° C. for the initial denaturation, and then, 45 cycles of 1 sec at 95° C. for denaturation, 30 sec at 58° C. for annealing and 30 sec at 72° C. for extension.

Figure 2:
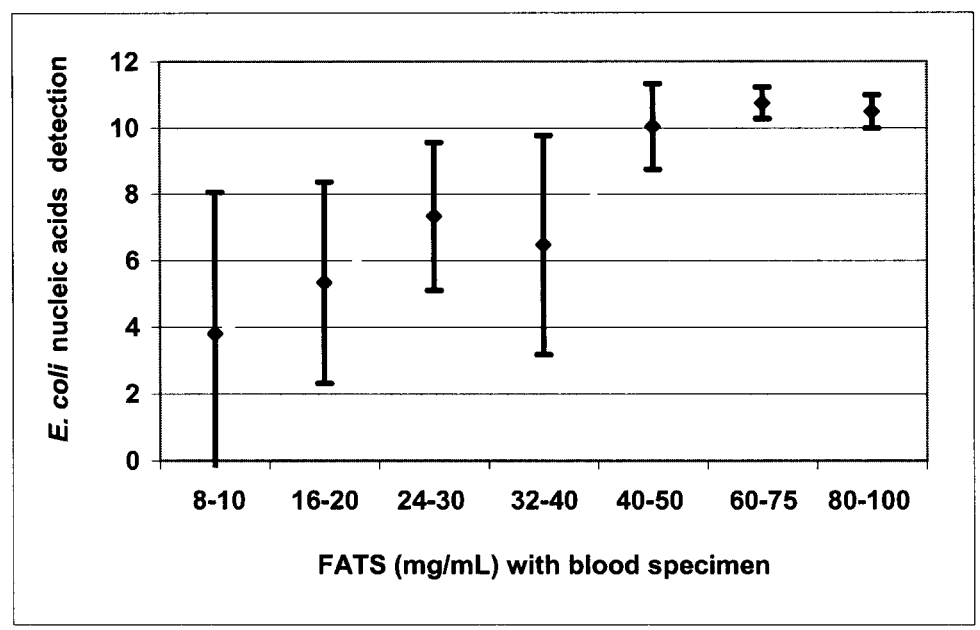
FIG. 2 shows *E. coli* nucleic acids detection according to final saponin concentration (two-step method). The relative efficiency of *E. coli* detection was estimated by calculating the difference between the cycle threshold value obtained for a blood sample treated with TE 1× and the cycle threshold values obtained for blood treated with different ranges of FATS concentrations. Standard deviations from the FATS-treated samples are for 4-10 repeats performed on at least three different treated blood samples. Nucleic acid detection increases with FATS concentration.

As shown in FIG. 2, *E. coli* nucleic acids detection increases with FATS concentration. *E coli* nucleic acids detection was increased between 60-100 mg/mL final FATS concentration. Similarly, microorganisms nucleic acids detection increased with HFATS concentration. Microorganisms nucleic acids detection was optimized at around about 80 mg/mL of HFATS. As shown in TABLE 1, *E. coli* nucleic acids detection correlation with increasing FATS concentration is associated with a reduction of the blood pellet volume. This reduction in the residual pellet volume starts at around 40 mg/mL of FATS. With HFATS, the residual pellet volume is consistently small (equivalent to the one obtained with 60-100 mg/mL FATS), even with the lowest HFATS concentrations. Considering that control experiments showed that smaller pellets appear to ease the harvesting of microbial cells and their nucleic acids, saponin concentrations of about 75 mg/mL or more may be advantageously used.

TABLE 1

INFLUENCE OF SAPONIN CONCENTRATION
ON WASHED PELLET SIZE

| | FATS (mg/mL) with blood specimen | | | | | | | |
|---|---|---|---|---|---|---|---|---|
| | 0-0 | 8-10 | 16-20 | 24-30 | 32-40 | 40-50 | 60-75 | 80-100 |
| Pellet volume (µL) | 100 | 50-75 | 50-75 | 50-75 | 30-50 | 30-50 | 20-40 | 10-20 |

Example 4

Detection of a Variety of Bacterial and Fungal Species

Detection of a variety of bacterial and fungal microorganisms was tested by PCR following their recovery from spiked blood specimens treated using methods of this invention (one-step and two-step methods). 5 mL of whole blood was inoculated with bacterial or yeast cell suspension. The two-step method was processed as follows. 15 mL of 100 mg/mL HFATS in TE 1x was added to the spiked blood sample and mixed for 10 seconds using a vortex set at maximum speed. Subsequently, the solution was centrifuged at 10 000 g for 5 minutes, and the supernatant was discarded. Then, 10 mL of 100 mg/mL HFATS in TE 1× was added to the pellet and mixed for 10 seconds using a vortex set at maximal speed. The suspension was then centrifuged at 10 000 g for 5 minutes and the supernatant was discarded. The one-step method was processed as follows: 20 mL of HFATS in TE 1× was added to the spiked blood and mixed for 10 seconds using a vortex set at maximum speed. Subsequently, the solution was centrifuged at 10 000 g for 5 minutes and the supernatant was discarded. The pellet was washed twice. 50 µL of TE 1× was added to the washed pellet. The washed pellet and TE 1× were vigorously shaken for 15 seconds using a vortex set at maximum speed. The pellet was removed by using a micropipette tip. The remaining suspension containing microbial cells was mechanically lysed with glass beads to extract microbial nucleic acids. For each target microbial species spiked into blood specimens, one blood donor was tested with a minimum of 2 replicas. Microbial nucleic acids were detected using multiplex PCR assays on a Rotor-Gene™ thermocycler (Corbett Life Science). These multiplex PCR tests incorporate primers specific to tuf, recA, and/or tef1 gene sequences as shown in TABLE 2.

TABLE 2

LIST OF SELECTED AMPLIFICATION PRIMERS AND PROBES

| Primers/probes combinations | SEQ ID NO. | Sequence | Target or source species |
|---|---|---|---|
| E. faecalis | 1 | ACTTGTCCACGTTSGATRTCT | Enterococcus faecalis |
|  | 2 | AATTAATGGCTGCWGTTGAYGAA | Enterococcus faecalis |
|  | 3 | ATCCCAACTCCAGAACGTGAYA | Enterococcus faecalis |
| E. coli | 4 | TGGGAAGCGAAAATCCTG | Escherichia coli |
|  | 5 | CAGTACAGGTAGACTTCTG | Escherichia coli |
|  | 6 | AACTGGCTGGCTTCCTGG | Escherichia coli |
| Multiplex #1 | 7 | ACTGGYGTTGAIATGTTCCGYAA | Broad-spectrum * |
|  | 8 | ACGTCAGTIGTACGGAARTAGAA | Broad-spectrum * |
|  | 9 | ACAGGTGTTGAAATGTTCCGTAA | Enterococcus faecalis |
|  | 10 | ACGTCTGTTGTACGGAAGTAGAA | Enterococcus faecalis |
|  | 11 | CAGGAATCGAAATGTTCAGAAAG | Clostridium perfringens |
|  | 12 | ACGTCTGTTGTTCTGAAGTAGAA | Clostridium perfringens |
|  | 13 | ACCTCCATCGAGATGTTCAACAA | Corynebacterium jeikeium |
|  | 14 | GGTGGTGCGGAAGTAGAA | Corynebacterium jeikeium |
|  | 15 | ACAGGAGTTGAGATGTTCCGTAA | Capnocytophaga canimorsus |
|  | 16 | ACGTCAGTTGTACGAACATAGAA | Capnocytophaga canimorsus |
| Multiplex #2 | 17 | GGTWGTIGCTGCGACTGACGG | Broad-spectrum * |
|  | 18 | TCAATCGCACGCTCTGGTTC | Broad-spectrum * |
|  | 19 | AACGTGGTCAAGTWTTAGC | Staphylococcus sp. |
|  | 20 | GTACGGAARTAGAATTGWGG | Staphylococcus sp. |
|  | 21 | GTGGRATIGCIGCCTTTATCG | Streptococcus sp. |
|  | 22 | ATIGCCTGRCTCATCATACG | Streptococcus sp. |
| Multiplex #3 | 23 | CAAGATGGAYTCYGTYAAITGGGA | Candida sp. |
|  | 24 | CATCTTGCAATGGCAATCTCAATG | Candida sp. |
|  | 25 | CATCTTGTAATGGTAATCTTAATG | Candida krusei |
|  | 26 | GTTCCAGACYICCAAGTATGAG | Aspergillus sp. |
|  | 27 | ATTTCGTTGTAACGATCCTCGGA | Aspergillus sp. |
|  | 28 | GATTTCGTTGTAACGATCCTGAGA | Aspergillus flavus |
|  | 29 | ATTTCGTTGTAACGGTCCTCAGA | Aspergillus terreus |
| Multiplex #4 | 30 | TGATGCCGRTIGAAGACGTG | Broad-spectrum * |
|  | 31 | AGYTTGCGGAACATTTCAAC | Broad-spectrum * |
|  | 32 | GTGGGAAGCGAAAATCCTG | Escherichia coli + Shigella sp. |

* Broad-spectrum primers where chosen for their capacity to amplify many bacterial species.

In accordance with the International Union of Biochemistry (IUB), the following nucleotide bases single letter codes have been used: A: Adenine (A), C: Cytosine (C), G: Guanine (G), T: Thymine (T), U: Uridine (U), and I: Inosine (I). Inosine is a modified base that can bind with any of the regular base (A, T, C or G). Inosine is used in order to minimize the number of degeneracies in an oligonucleotide. For sequence degeneracies the IUB codes are M: Adenine or Cytosine (A or C), R: Adenine or Guanine (A or G), W: Adenine or Thymine (A or T), S: Cytosine or Guanine (C or G), Y: Cytosine or Thymine (C or T), and K: Guanine or Thymine (G or T).

Oligonucleotide sequence of primers or probes may be derived from either strand of the target duplex DNA. The primers or probes may consist of the bases A, G, C, or T or analogs and they may be degenerated at one or more chosen nucleotide position(s) to ensure DNA amplification for all strains of a target bacterial and/or fungal species. Degenerated primers are primers which have a number of possibilities at mismatch positions in the sequence in order to allow annealing to complementary sequences and amplification of a variety of related sequences. For example, the following primer AYATTAGTGCTTTTAAAGCC is an equimolar mix of the primers ACATTAGTGCTTTTAAAGCC and A TATTAGTGCTTTTAAAGCC. Degeneracies reduce the specificity of the primer(s), meaning mismatch opportunities are greater, and background noise increases; also, increased degeneracy means concentration of the individual primers decreases; hence, greater than 512-fold degeneracy is preferably avoided. Thus, degenerated primers should be carefully designed in order to avoid affecting the sensitivity and/or specificity of the assay. Several primers have been designed to efficiently amplify the pathogens described herein. Each of the individual oligonucleotides possess their own utility; it may be possible to use such oligonucleotides for other purposes than those described herein. For example, primers used in the present invention may be combined with other primers for amplification of a longer or shorter amplicon; probes used in the present invention may be combined with other probes.

PCR tests were conducted to assess the detection of selected species at low microbial cell concentrations. PCR reactions were performed in a 25 µL mixture containing 2.5 µL of lysate with the concentrated microbial nucleic acids, 1×PC2 buffer (Ab Peptides) (1× PC2 is 50 mM Tris-HCl at pH 9.1, 16 mM $(NH_4)_2SO_4$, 3.5 mM $MgCl_2$, 0.150 mg/mL bovine serum albumine), 0.4 to 1.2 µM of each primers (optimal concentration for each primer was adjusted to ensure maximum amplification yield), 0.2 mM each of the four dinucleotide triphosphate (dNTPs) mix (GE Healthcare) and 0.05 to 0.06 U/µL of KlenTaq1™ DNA polymerase (Ab Peptides), coupled with TaqStart® antibody (Clontech Laboratories). The PCR reaction mixture was supplemented with $MgCl_2$ (Promega) so that the final magnesium chloride concentration was 4.5 mM, and with bovine serum albumin (BSA) fraction V (Sigma) so that the final BSA concentration was 2.15 mg/mL. Also, 8-methoxypsoralen (8-Mop) (Sigma) was added to the reaction master mix at 0.13 µg/µL and exposed to UV illumination in a Spectrolinker™XL-1000 (Spectronics Corp.) between 9999 and 40 000 µJ/cm² in order to control DNA contamination. UV exposure was adjusted according to the level of contamination of the different reagent lots as described in WO03087402. For post-PCR detection of amplicons by melting-curve analysis, the PCR mixture described above was supplemented with 1× SYBR® Green (Molecular Probes), and the different melting temperatures of the amplicons were determined according to the instruction provided by the thermocycler's manufacturer. Thermocycling conditions using the Rotor-Gene™ apparatus were 1 min at 95° C., for the initial denaturation, and then 40 cycles of 1 sec at 95° C. for denaturation, 10 sec at 60° C. for annealing, and 20 sec at 72° C. for extension. The amplicons were melted using a temperature range of 60° to 95° C.

As shown in TABLE 3, the analytical sensitivity ranged from 1 to 47 CFU/mL (for the one-step method) or from 1 to 25 CFU/mL (for the two-step method). The analytical sensitivity also depended on the target bacterial and fungal species spiked in blood samples.

When the method of the present invention is compared with data reported for 24 microbial species covered by SeptiFast test from Roche Diagnostics (Lehmann et al, 2007, Med. Microbiol. Immunol. 197:313-24), analytical sensitivities were at least equivalent. It is important to note that the SeptiFast test requires a blood sample preparation protocol more complex and much longer than the method of the present invention.

TABLE 3

BACTERIAL AND FUNGAL SPECIES RECOVERED AT LOW CELL CONCENTRATIONS FROM SPIKED BLOOD SPECIMENS TREATED USING THE METHODS OF THIS INVENTION

| | Analytical sensitivity* in CFU/ml of blood (lowest cellular load tested) | |
|---|---|---|
| Bacterial species | One-step method | Two-step method |
| Acinetobacter baumannii | 3 (3) | 1 (1) |
| Bacteroides fragilis | 30 (15) | 15 (15) |
| Burkholderia cepacia | NT | 5 (5) |
| Citrobacter freundii | 2.5 (1) | 1 (1) |
| Citrobacter koseri | 7 (7) | 7 (7) |
| Enterobacter aerogenes | 2 (2) | 10 (10) |
| Enterobacter cloacae | 3 (3) | 12 (12) |
| Enterococcus faecalis | 2 (2) | 14 (14) |
| Enterococcus faecium | 4 (4) | 7 (7) |
| Escherichia coli | 15 (15) | 6 (6) |
| Haemophilus influenzae | 9 (9) | 5 (5) |
| Klebsiella oxytoca | 3 (3) | 19 (19) |
| Klebsiella pneumoniae | 3 (3) | 3 (3) |
| Proteus mirabilis | 11 (11) | 2 (2) |
| Pseudomonas aeruginosa | 17 (1) | 6 (6) |
| Serratia marcescens | 10 (10) | 1 (1) |
| Staphylococcus aureus | 8 (8) | 15 (8) |
| Staphylococcus epidermidis | 9 (5) | 19 (5) |
| Staphylococcus haemolyticus | 1 (1) | 1 (1) |
| Staphylococcus hominis | 4 (4) | 4 (4) |
| Staphylococcus warneri | 14 (14) | 3 (3) |
| Stenotrophomonas maltophilia | 7 (7) | 7 (7) |
| Streptococcus agalactiae | 19 (19) | 12 (12) |
| Streptococcus anginosus | 16 (16) | 7 (7) |
| Streptococcus dysgalactiae | 14 (5) | 14 (5) |
| Streptococcus mutans | 20 (10) | 10 (10) |
| Streptococcus pneumoniae | 6 (6) | 6 (6) |
| Streptococcus pyogenes | 47 (25) | 25 (25) |
| Streptococcus sanguinis | 9 (9) | 6 (6) |
| Candida albicans | NT | 8 (8) |
| Candida glabrata | NT | 14 (14) |
| Candida krusei | NT | 17 (17) |
| Candida parapsilosis | NT | 15 (15) |
| Candida tropicalis | NT | 10 (10) |
| Aspergillus fumigatus | NT | 10 (10) |

*Detection was performed by PCR amplification on a Rotor-Gene ™ thermocyler and amplicons were characterized by SYBR Green melting curve analysis. NT: not tested.

Example 5

Concentration and Enrichment of Viable Microbial Cells from Blood with a Low Load of Microbial Cells The viability of microbial cells following their recovery from spiked blood specimens with a low load of microbial cells using the method of this invention was examined. 5 mL of whole blood samples were inoculated with approximately 2, 10 or 20 CFU of *Streptococcus pneumoniae* per mL in three replicates. The spiked blood was treated with saponin using the single treatment method as described above and as follows. 20 mL of 100 mg/mL HFATS in TE 1× was added to spiked blood samples and mixed for 10 seconds using a vortex set at maximum speed. Pelleted blood residues and microbial cells were obtained by centrifugation at 10 000 g for 5 minutes and the supernatant was discarded. The pellet was washed in 1.7 mL of PBS 1× by mechanically disrupting the pellet by up and down pipetting and mixed for 10 seconds using a vortex at maximum speed. The suspension was centrifuged at 10 000 g for 1 minute and the supernatant was discarded. This washing step was repeated once. 60 µL of PBS 1× (rinsing and harvesting solution) was added to the washed pellet and vigorously shaken for 15 seconds using a vortex set at maximum speed.

The pellet was mechanically removed by using a micropipette tip and either transferred to 3 mL of enriched brain hearth infusion broth (eBHI) or to a new tube containing 25 µL of PBS 1×. PBS 1× containing the pellet was subsequently plated on blood agar media. The total harvested aqueous suspension comprising the harvested microbial cells was either transferred to 3 mL of eBHI or on blood agar media for plating.

Plates and broths were incubated at 35° C. with 5% $CO_2$ atmosphere overnight for CFU counts determination and growth evaluation. Viable bacterial cells were recovered from the aqueous suspension even when as few as 10 CFU of *S. pneumoniae* were present in the initial 5 mL blood sample (i.e. 2 CFU/mL). Viable bacterial cells were could also be recovered from the pellet. Moreover, these recovered bacterial cells are able to grow on blood agar media as well as in eBHI.

Viable *Candida albicans, Escherichia coli, Klebsiella oxytoca, Haemophilus influenzae* and *Staphylococcus aureus* microbial cells were also recovered when blood was spiked with a low cellular load of these five other microorganisms.

These results show that the method of the present invention allows recovery of a high percentage of viable cells even when a low load of microorganisms is used to spike a blood sample. These results, obtained with viable cells from harvested aqueous suspension or the pellet, are reproducible within a range of 0.2 to 22 CFU per mL of blood.

Example 6

Concentration and Enrichment of Viable Microbial Cells from Blood with a High Load of Microbial Cells The viability of microbial cells following their recovery from spiked blood specimens with a high load of microbial cells using the method of this invention was examined. Three replicates of 5 mL of whole blood samples were inoculated with 10 700 CFU of *Escherichia coli* per mL. The spiked blood was treated with the one-step method as described above and as follows. 20 mL of 100 mg/mL HFATS in TE 1× was added to spiked blood samples and mixed for 10 seconds using a vortex set at maximum speed. Pelleted blood residues and microbial cells were obtained by centrifugation at 10 000 g for 5 minutes and the supernatant was discarded.

The pellet was washed in 1.7 mL of PBS 1× by mechanically disrupting the pellet with up and down pipetting and mixed for 10 seconds using a vortex at maximum speed. 100 µL of the suspension was transferred in a new tube to further proceed to serial dilutions in PBS 1×. Three replicates of the $10^{-1}$ dilution were plated on blood agar media. 5 µL of the non diluted suspension were transferred in 3 mL of eBHI. The remaining suspension was centrifuged at 10 000 g for 1 minute and the supernatant was discarded. The washing, sampling and processing steps were repeated once.

60 µL of TE 1× (rinsing and harvesting solution) was added to the washed pellet and mixed for 15 seconds using a vortex set at maximum speed. The pellet was mechanically removed by using a micropipette tip and either transferred to 3 mL of eBHI in triplicates or to a new tube containing 25 µL of PBS 1× in triplicates. PBS 1× containing the pellet was subsequently plated on blood agar media. 30 µL of the total aqueous phase comprising the harvested microbial cells were transferred in a new tube to further proceed to serial dilutions in PBS 1×. Three replicates of each serial dilution were plated on blood agar media. 5 µL of the non diluted suspension were transferred in 3 mL of eBHI.

Plates and broths were incubated at 35° C. for CFU count determinations. The results showed that after the first and second washing steps, microbial cells were recovered at an average of 106%±27% and 117%±19%, respectively. These percentages represent the ratio between the number of viable *E. coli* cells recovered at each step versus the number of viable *E. coli* cells initially inoculated in the blood sample. After the final step, 85%±18% of viable *E. coli* cells were recuperated. These results show that a high proportion of viable bacterial cells were recovered from each washing suspension as well as from the rinsing/harvesting final suspension. Moreover, these recovered bacterial cells are able to grow in eBHI. These results show that methods of the present invention allow recovery of a high percentage of viable cells at any step during sample processing.

Although the present invention has been described by way of exemplary embodiments, it should be understood by those skilled in the art that the foregoing and various other changes, omissions and additions may be made therein and thereto, without departing from the spirit and scope of the present invention as defined in the appended claims.

REFERENCES

EPO Publication No. 0,745,849
EPO Publication No. 1,422,509
U.S. Pat. No. 3,883,425
U.S. Pat. No. 4,164,449
U.S. Pat. No. 5,645,992
WO 03087402
Al-SOud et al., 2000, J. Clin. Microbiol., 39:485-493
Barr, et al., 1998, Ad Drug Deliv Rev, 32: 247-271
Bernhardt et al., 1991, J. Clin. Microbiol., 29:422-425
Bougnoux et al., 1999, J. Clin. Microbiol., 37:925-930
Carter-Wallace, Inc., Cranbury, N.J. 08512-0181
Cockerill et al., 1996, J. Clin. Microbiol., 34:20-24
Daar et al., 2002, Nat. Genet., 32:229-232
Francis et al., 2002, British J of Nutrition, 88: 587-605
Grossi et al., 2006, Surg. Infect. (Larchmt) 7:S87-S91
Güçlü-Üstündag, Ö., et al., 2007, Crit. Rev Food Sci Nut: 231-258
Henry et al., 1983, J. Clin. Microbiol., 17:864-869
Hoorfar et al., 2004, J. Appl. Microbiol., 96:221-222
Hoorfar et al., 2004, Lett. Appl. Microbiol., 38:79-80
Jonsson et al., 1993, APMIS, 101:595-601
Jordan et al, 2005, J. Mol. Diagn., 7:575-581
Kiehn et al., 1983, J. Clin. Microbiol., 18:300-304
Leconte et al. 1997, Phytochem., 44:575-579
Lehmann et al, 2007, Med. Microbiol. Immunol. 197:313-24
Link et al., 2007, Nat. Rev. Microbiol. 5:680-688;
Loeffler et al., 2002, J. Clin. Microbiol., 40:2240-2243
McLaughlin et al. 1983, J. Clin. Microbiol., 18:1027-1031

Melzig, et al. 2001, Planta Med., 67:43-48
Metzger, S. et al, ASM general meeting 2008, Abstract C-005
Metzger, S. et al, ASM general meeting 2008, Abstract C-145
Milgate et al. 1995, Nutrition Research, 15, no. 8; 1223-1249
Mitra et al., 1997, J. Agric. Food Chem., 45:1587-1595
Murray et al., 1991, J. Clin. Microbiol., 29:901-905
Okubo, K. et al, Oxygen-Saponins used in food and agriculture Plenum Press, NY, 1996
San Martin et al., 2000, J. Sci. Food Agric., 80:2063-2068
Takechi et al. 2003, Phytother. Res., 17:83-85
Taylor, 1994, Eur. J. Clin. Microbiol. Infect. Dis., 13:249-252
Weibel et al., 2007, Nat. Rev. Microbiol. 5:209-218
White et al., 2006, Clin. Infect. Dis., 42:479-486

The invention claimed is:

1. A method for isolating bacteria and/or bacterial nucleic acids from a blood sample comprising or suspected of comprising bacteria, the method comprising:
   a. contacting the blood sample with a saponin formulation, wherein the saponin is a filtered autoclaved-treated saponin solution (FATS) or a heated filtered autoclaved-treated saponin solution (HFATS) present at a final concentration of 40 mg/ml to 100 mg/ml; and
   b. obtaining isolated bacteria;
whereby the isolated bacteria comprises nucleic acids.

2. The method of claim 1, wherein the isolated bacterial are viable and/or metabolically active.

3. The method of claim 1, wherein the final concentration of saponin is from 75 mg/mL to 100 mg/mL.

4. The method of claim 1, wherein said saponin formulation comprises saponin selected from the group consisting of steroidal saponin, triterpenoid saponin and combination thereof.

5. The method of claim 1, wherein the saponin formulation is a triterpenoid saponin formulation.

6. The method of claim 1, wherein the blood sample is a human blood sample.

7. The method of claim 1, wherein obtaining isolated microorganisms comprises at least one centrifugation and or filtration step.

8. The method of claim 1, wherein said method provides for isolation of bacteria present at a concentration as low as 0.2 to 22 CFU per mL of blood.

9. The method of claim 1, wherein the bacteria are selected from the group consisting of *Enterococcus faecalis*, *Enterococcus faeciwn*, *Escherichia coli*, *Haemophilus influenzae*, *Klebsiella oxytoca*, *Klebsiella pneumoniae*, *Proteus mirabilis*, *Pseudomonas aeruginosa*, *Serratia marcescens*, *Staphylococcus aureus*, *Staphylococcus epidermidis*, *Staphylococcus haemolyticus*, *Staphylococcus hominis*, *Staphylococcus warneri*, *Stenotrophomonas maltophilia*, *Streptococcus agalactiae*, *Streptococcus anginosus*, *Streptococcus dysgalactiae*, *Streptococcus mutans*, *Streptococcus pneumoniae*, *Streptococcus pyogenes*, *Streptococcus sanguinis* and combination thereof.

10. The method of claim 1, wherein the bacteria are bacteria which may cause a bloodstream infection.

11. The method of claim 1, whereby the isolated bacteria are substantially free of amplification inhibitors.

12. The method of claim 1, further comprising lysing the isolated bacteria and isolating therefrom nucleic acids.

13. The method of claim 12, further comprising amplifying said nucleic acids.

14. A method for detecting bacteria in a blood sample, comprising:
   a. contacting a blood sample with a saponin formulation to a final concentration of saponin in a range of 75 mg/mL to 100 mg/mL, wherein said saponin formulation is a heated filtered autoclaved-treated saponin (HFATS) solution;
   b. isolating bacteria having nucleic acids by using at least one centrifugation and/or at least one filtration step; and
   c. assessing the presence of isolated bacteria having nucleic acids.

15. The method of claim 14, wherein assessing the presence of isolated bacteria comprises amplifying nucleic acids from said bacteria.

16. The method of claim 14, wherein said bacteria are present in the blood sample at a concentration as low as 0.2 to 22 CFU per mL of blood.

17. A method for obtaining nucleic acids from bacteria present in a blood sample, the method comprising:
   a. contacting the blood sample with a saponin formulation, wherein saponin is a filtered autoclaved-treated saponin solution (FATS) or a heated filtered autoclaved-treated saponin solution (HFATS) present at a final concentration of 40 mg/ml to 100 mg/ml;
   b. obtaining isolated bacteria comprising nucleic acids; and c. lysing the isolated bacteria for obtaining therefrom nucleic acids.

18. The method of claim 17, wherein obtaining isolated bacteria comprises at least one centrifugation and/or at least one filtration step.

19. The method of claim 18, further comprising amplifying nucleic acids from said bacteria for identification and/or diagnostic purposes.

20. A method for diagnosing a blood infection in a subject in need thereof comprising:
- a) contacting a blood sample from said subject with a saponin formulation using techniques and conditions where microorganisms comprising nucleic acids are isolated from host cells and host cell debris, wherein saponin is a filtered autoclaved-treated saponin solution (FATS) or a heated filtered autoclaved-treated saponin solution (HFATS) present at a final concentration of 40 mg/ml to 100 mg/ml; and
- b) assessing presence or absence of bacteria comprising nucleic acids; whereby detection of bacteria comprising nucleic acids is indicative of an infection associated with the bacteria detected.

\* \* \* \* \*